US010405997B2

(12) United States Patent
Arelekatti et al.

(10) Patent No.: US 10,405,997 B2
(45) Date of Patent: Sep. 10, 2019

(54) PASSIVE ARTIFICIAL KNEE

(71) Applicant: Massachusetts Institute of Technology, Cambridge, MA (US)

(72) Inventors: Venkata Narayana Murthy Arelekatti, Cambridge, MA (US); Amos G. Winter, Cambridge, MA (US); Daniel Scott Dorsch, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/571,027

(22) PCT Filed: May 4, 2016

(86) PCT No.: PCT/US2016/030779
§ 371 (c)(1),
(2) Date: Oct. 31, 2017

(87) PCT Pub. No.: WO2016/179281
PCT Pub. Date: Nov. 10, 2016

(65) Prior Publication Data
US 2018/0161180 A1 Jun. 14, 2018

Related U.S. Application Data

(60) Provisional application No. 62/156,956, filed on May 5, 2015.

(51) Int. Cl.
*A61F 2/64* (2006.01)
*A61F 2/68* (2006.01)
(Continued)

(52) U.S. Cl.
CPC ........ *A61F 2/64* (2013.01); *A61F 2002/5003* (2013.01); *A61F 2002/5006* (2013.01);
(Continued)

(58) Field of Classification Search
CPC ...... A61F 2002/6845; A61F 2002/6854; A61F 2005/0162; A61F 2/64
(Continued)

(56) References Cited

U.S. PATENT DOCUMENTS 5,545,232 A 8/1996 Van de Veen
5,645,590 A 7/1997 Van de Veen
(Continued)

FOREIGN PATENT DOCUMENTS

EP   1 186 279 A1 * 3/2002 ........... A61F 5/0125
WO   WO 2012/166853 A1   12/2012

OTHER PUBLICATIONS

"Guidelines for Training Personnel in Developing Countries for Prosthetics and Orthotics Services," World Health Org., 2005.
(Continued)

*Primary Examiner* — David H Willse
(74) *Attorney, Agent, or Firm* — Sunstein Kann Murphy & Timbers LLP

(57) ABSTRACT

A passive artificial knee includes a knee hinge assembly defining a knee axis, a locking hinge assembly defining a locking axis, and a post linking the knee hinge assembly and the locking hinge assembly. A ground reaction force applied to the artificial knee posterior to the locking axis causes an interfering relation by compression of the locking hinge assembly and the knee hinge assembly during heel strike at early-stance gait phase of an individual wearing the artificial knee, thereby locking rotation of the post about the knee axis. Shifting of ground reaction force anterior to the locking axis during a mid-stance to late-stance gait phase of the individual causes rotation of the post about the locking axis, thereby unlocking rotation of the post about the knee axis and enabling flexion and subsequent swing phase extension of the passive artificial knee joint. The artificial knee is a (Continued)

passive joint that can be fabricated and maintained at low expense.

13 Claims, 11 Drawing Sheets

(51) Int. Cl.
    *A61F 2/50*         (2006.01)
    *A61F 5/01*         (2006.01)

(52) U.S. Cl.
    CPC .............. *A61F 2002/5043* (2013.01); *A61F 2002/5073* (2013.01); *A61F 2002/6845* (2013.01); *A61F 2002/6854* (2013.01); *A61F 2005/0162* (2013.01)

(58) Field of Classification Search
    USPC .......................................................... 623/44
    See application file for complete search history.

(56) References Cited

U.S. PATENT DOCUMENTS

| | | |
|---|---|---|
| 7,087,090 B2 | 8/2006 | Andrysek et al. |
| 7,909,885 B2 | 3/2011 | Andrysek |
| 7,918,898 B2 | 4/2011 | Andrysek |
| 2005/0149203 A1 | 7/2005 | Andrysek et al. |

OTHER PUBLICATIONS

"World Report on Disability," World Health Org., 2011.
Andrysek, J., "LC Knee™," at least as early as May 4, 2016.
Andrysek, J., "Lower-limb prosthetic technologies in the developing world: A review of literature from 1994-2010," *Prosthet. Orthot. Int.*, vol. 34, No. 4, pp. 378-398 (2010).
Arelekatti, V.N.M ., et al., "Design and Preliminary Field Validation of a Fully Passive Prosthetic Knee Mechanism for Users with Transfemoral Amputation in India," ASME J. Mech. & Robotics, 23 pages. (Feb. 5, 2018).
Arelekatti, V.N.M ., et al., "Draft: Design of a Passive Prosthetic Knee Mechanism for Users With Transfemoral Amputation in India," Proc. ASME 2016 Inter'l Design Eng. Tech. Conf., Aug. 21-24, 2016, Charlotte, US (9 pages).
Arelekatti, V.N.M., et al., "Design of a Fully Passive Prosthetic Knee Mechanism for Transfemoral Amputees in India", *IEEE Int'l Conf Rehab. Robotics*, 350-356 (2015).
Blumentritt, et al., "Design Principles, Biomechanical Data and Clinical Experience with a Polycentric Knee Offering Controlled Stance Phase Knee Flexion: A Preliminary Report," J. of Prosthetics and Orthotics, vol. 9, No. 1, p. 18 (1997).
Cummings, D., "Prosthetics in the developing world: a review of the literature," *Prosthet. Orthot. Int.*, vol. 20, No. 1, pp. 51-60 (1996).
Hamner, S. et al., "Designing for Scale: Development of the ReMotion Knee for Global Emerging Markets," *Ann. Biomed. Eng.*, vol. 41, No. 9, pp. 1851-1859 (2013).
International Search Report and Written Opinion for Int'l Application No. PCT/US2016/030779, titled: Passive Artificial Knee, dated Jul. 20, 2016.
Narang, Y. S. and A.G. Winter, Aug. 2014, "Effects of prosthesis mass on hip energetics, prosthetic knee torque, and prosthetic knee stiffness and damping parameters required for transfemoral amputees to walk with normative kinematics," In ASME 2014 International Design Engineering Technical Conferences and Computers and Information in Engineering Conference, vol. 5A: *38th Mechanisms and Robotics IDETC Conference*, 2014. (pp. V05ATO8A017-V05ATO8A017).
Narang, Y., "Identification of design requirements for a high-performance, low-cost, passive prosthetic knee through user analysis and dynamic simulation," M.S. thesis, Dept. Mech. Eng., Massachusetts Inst. of Technology, Cambridge, MA, 2013.
Notification Concerning Transmittal of International Preliminary Report on Patentability, PCT/US2016/030779, titled: Passive Artificial Knee, dated Nov. 7, 2017.

* cited by examiner

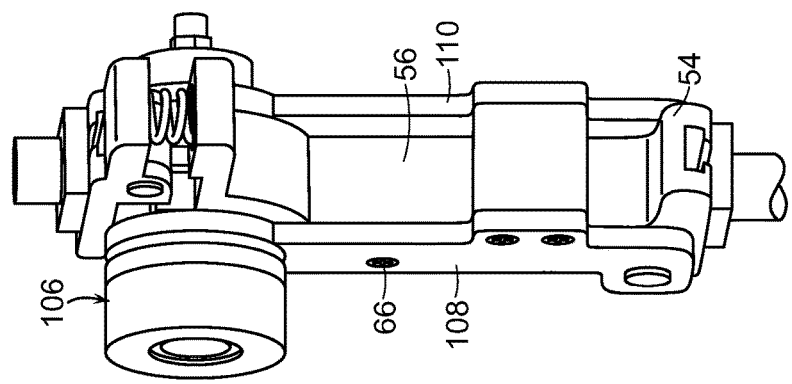
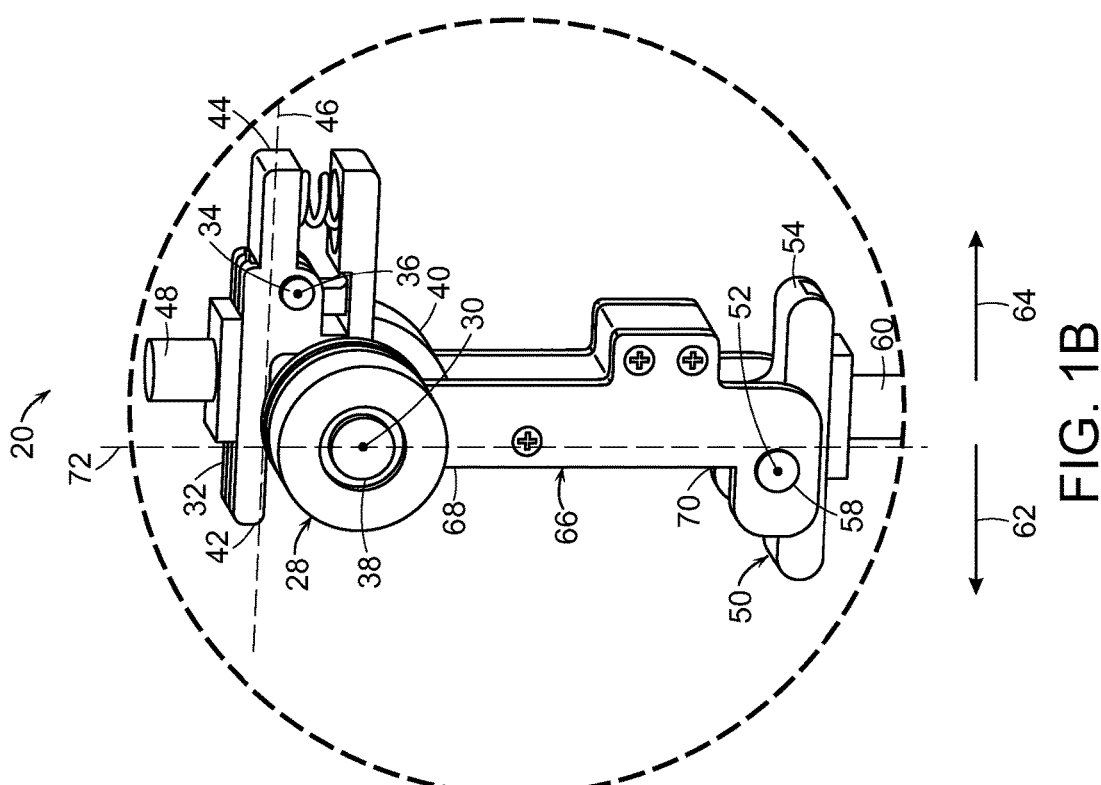

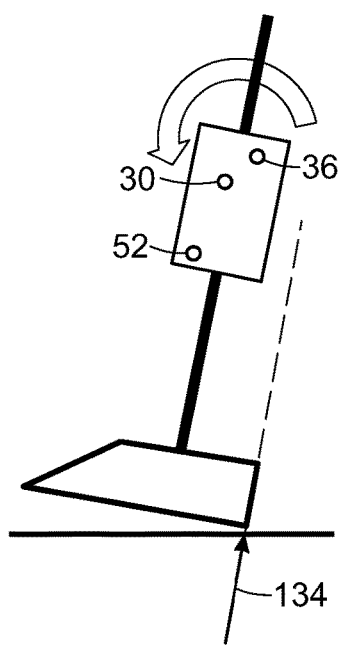
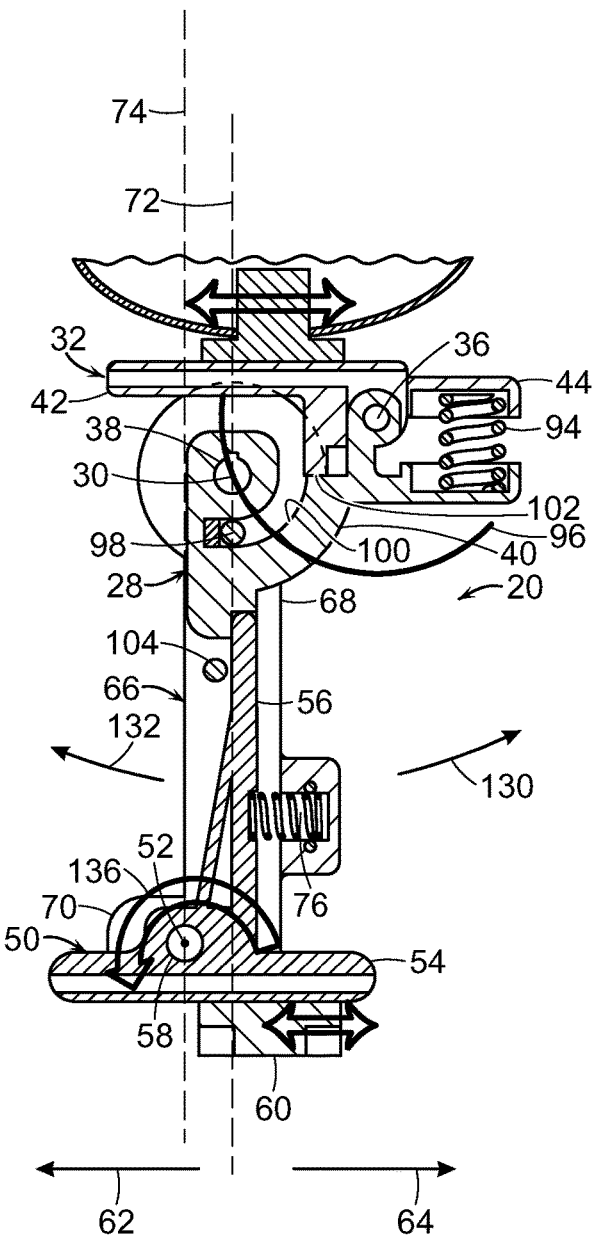
FIG. 2A
FIG. 2B

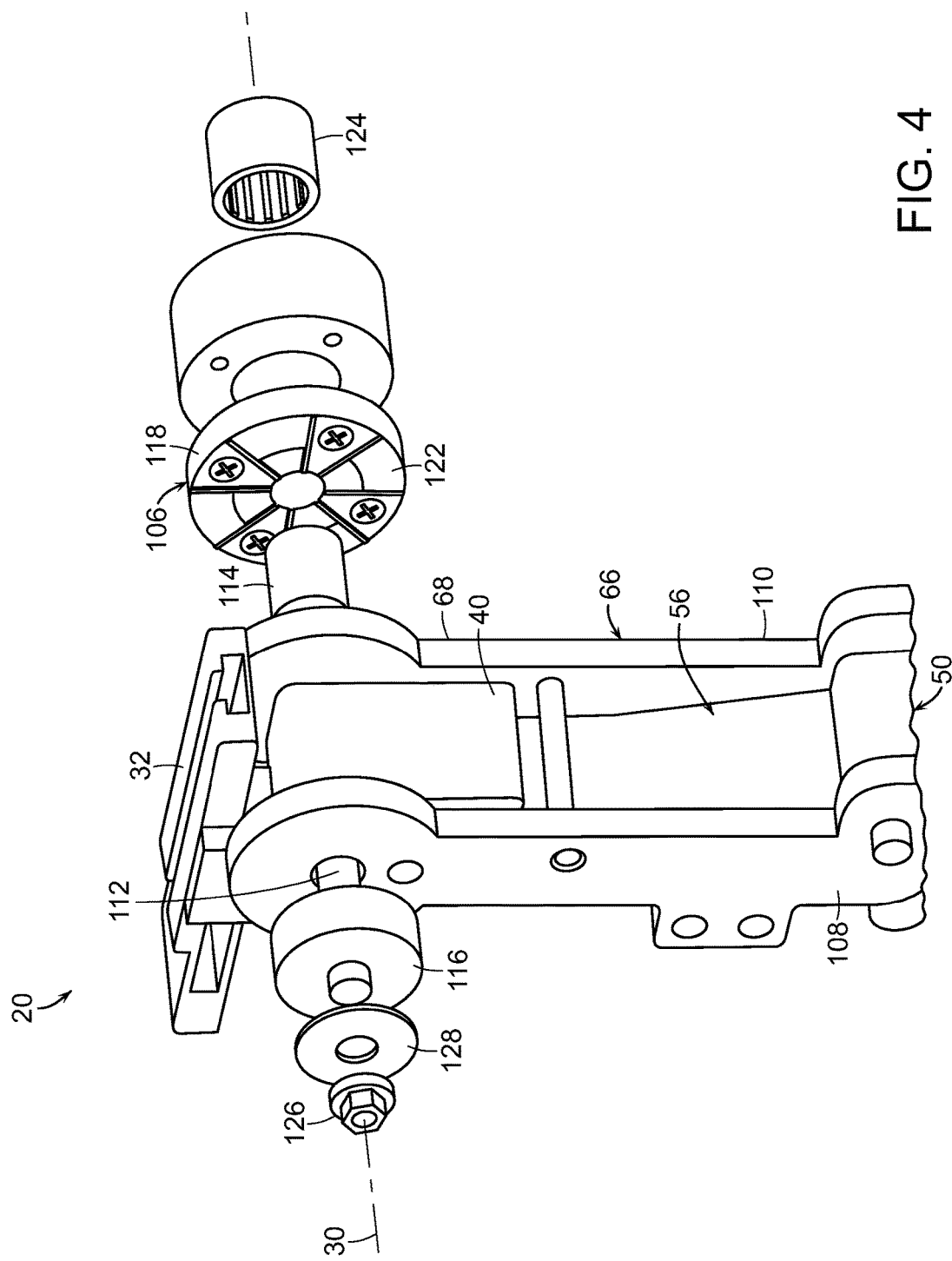

PASSIVE ARTIFICIAL KNEE

RELATED APPLICATION

This application is the U.S. National Stage of International Application No. PCT/US2016/030779, filed May 4, 2016, which designates the U.S., published in English, and claims the benefit of U.S. Provisional Application No. 62/156,956, filed on May 5, 2015. The entire teachings of the above applications are incorporated herein by reference.

BACKGROUND

It is estimated that across the world 30 million people are in need of prosthetic and orthotic devices. ("Guidelines for Training Personnel in Developing Countries for Prosthetics and Orthotics Services," World Health Org., 2005; "World Report on Disability," World Health Org., 2011; and S. Hamner, V. Narayan and K. Donaldson, "Designing for Scale: Development of the ReMotion Knee for Global Emerging Markets," *Ann. Biomed. Eng.*, vol. 41, no. 9, pp. 1851-1859, 2013, the relevant teachings of all of which are incorporated herein by reference in their entirety.)

A majority of amputees live in developing countries having large populations, such as India and China (Hamner et al.). According to an estimate by the World Health Organization, 90-95% of amputees in developing countries do not receive any prosthetic device (J. Andrysek, "Lower-limb prosthetic technologies in the developing world: A review of literature from 1994-2010," *Prosthet. Orthot. Int.*, vol. 34, no. 4, pp. 378-398, 2010, the relevant teachings of which are incorporated by reference in their entirety) and only 20% of the amputees are able to afford currently available prostheses in the market (D. Cummings, "Prosthetics in the developing world: a review of the literature," *Prosthet. Orthot. Int.*, vol. 20, no. 1, pp. 51-60, 1996, the relevant teachings of which are incorporated by reference in their entirety).

Current above-knee prostheses being distributed in the developing countries typically employ single-axis joints with or without manual locks. These prostheses often inhibit normative gait and suffer frequent mechanical failures resulting in low-user satisfaction (Andrysek et al).

Although a number of advanced prosthetic limbs and assistive devices have been designed in the developed world in the last few decades, very few of them have been suitable for large-scale use in developing countries due to vastly different and complex socio-economic considerations and resource-constrained settings. Passive knee joints commonly employed in developed countries, on the other hand, generally are considered to be too expensive to meet the requirements of amputees in the developing world.

Therefore, there is a need for a passive artificial knee that overcomes or minimizes the above-referenced problems.

SUMMARY OF THE INVENTION

The invention generally is directed to an artificial knee for a human being.

In one embodiment, the passive artificial knee of the invention includes a knee hinge assembly defining a knee axis, a locking hinge assembly defining a locking axis, and a post linking the knee hinge assembly and the locking hinge assembly, wherein a ground reaction force applied to the artificial knee posterior to the locking axis causes an interfering relation at a point between the locking hinge assembly and the knee hinge assembly during heel strike and early-stance gait phases of an individual wearing the artificial knee, whereby rotation of the knee hinge causes radial compression of the knee hinge assembly at the point of interfering relation, thereby locking rotation of the post about the knee axis, and wherein shifting of the ground reaction force anterior to the locking axis during a mid-stance gait phase of the individual causes rotation of the post about the locking axis, thereby unlocking rotation of the post about the knee axis.

In another embodiment of the invention, the artificial knee includes a head plate having anterior and posterior ends that together define a head plate axis, and an early-stance flexion hinge between the anterior end and the posterior end, and defining an early-stance flexion axis that is normal to the head plate axis. A post of the artificial knee includes a first end and a second end that together define a major longitudinal axis. A knee hinge of the post defines a knee axis at the first end of the post, wherein the knee axis is normal to and intersects the major longitudinal axis. A locking hinge of the post defines a locking axis at the second end of the post, wherein the locking axis is normal to and intersects a line parallel to the major longitudinal axis. A linking member is linked to the head plate at the early-stance flexion hinge and is also linked to the post at the knee hinge, wherein, when the major longitudinal axis of the post is normal to the head plate axis, the line parallel to the major longitudinal axis intersects the head plate axis on a side of the knee axis opposite to that of the early-stance flexion axis. A spring between the head plate and the linking member biases rotation of the linking member about the early-stance flexion axis to thereby direct the knee hinge and the first end of the post toward the head plate. A footplate is linked to the post at the locking hinge, which footplate includes a latch that is in an interfering relation at a point between the latch and the linking member at or posterior to the major longitudinal axis during heel strike and early-stance gait phases of an individual wearing the artificial knee, whereby the latch will be engaged with the linking member, thereby causing radial compression of the knee hinge assembly at the point of interfering relation and preventing rotation of the post about the knee axis, and whereby, during a mid-stance gait phase of the individual, when a ground reaction force applied to the artificial knee is anterior to the locking axis, the footplate will rotate about the locking axis and consequently disengage the latch from the linking member, thereby enabling the post to rotate about the knee axis.

Embodiments of this invention have many advantages. For example, the artificial knee of the invention enables a transfemoral amputee to realize able-bodied kinematics simultaneously with a minimum of metabolic energy expenditure. Also, radial compression at a point of interfering relation between the knee axis and the locking hinge assembly to thereby prevent rotation, or flexion of the knee significantly reduces the likelihood of catastrophic failure of the artificial knee. Further, the passive artificial knee of the invention is passive, thereby avoiding the need for an onboard energy source. Further, the artificial knee of the invention can be fabricated and maintained at very low cost, thereby having the potential to meet socio-economic, cultural and aesthetic needs of transfemoral amputees in developing countries.

BRIEF DESCRIPTION OF THE DRAWINGS

FIG. 1B is one perspective view of the artificial knee shown in FIG. 1A.

FIG. 1C is another perspective view of the artificial knee shown in FIGS. 1A and 1B.

FIG. 2A is a schematic representation of ground reaction force of heel strike of an artificial limb employing the artificial knee of the invention.

FIG. 2B is a cross-sectional view of the embodiment of the artificial knee shown in FIGS. 1A-1C showing the position of the artificial knee at heel strike as represented in FIG. 2A.

FIG. 4 is a perspective view of the knee hinge assembly and differential damping system of the embodiment of the artificial knee shown in FIGS. 1A-1C.

DETAILED DESCRIPTION OF THE INVENTION

Figure 1A:
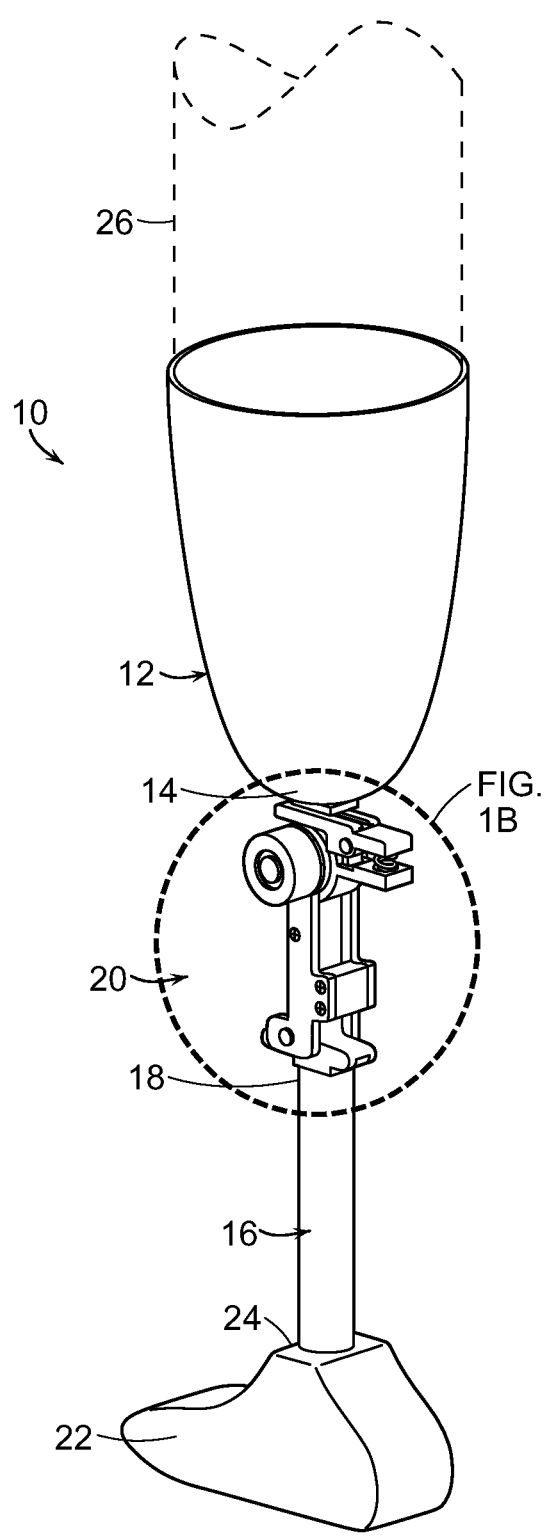
FIG. 1A is a perspective view of an artificial limb that includes one embodiment of an artificial knee of the invention.

The invention generally is directed to a passive artificial knee for human beings having a transfemoral amputation. The artificial knee of the invention is fully passive in that it does not require an onboard power source. Further, the artificial knee of the invention can be fabricated and maintained at relatively low cost.

In one embodiment, shown in FIG. 1, artificial limb 10 includes socket 12 having distal end 14, pylon 16 having proximal end 18, and artificial knee 20 of the invention linking socket 12 and pylon 16 at distal end 14 and proximal end 18, respectively. Prosthetic foot 22 is fixed to distal end 24 of pylon 16. Socket 12 is fitted to human 26 having a transfemoral amputation.

FIGS. 1B and 1C are perspective views of artificial knee 20 shown in FIG. 1A. As shown in FIGS. 1B and 1C, artificial knee 20 includes knee hinge assembly 28 defining knee axis 30. Knee hinge assembly 28 includes head plate 32, early-stance flexion hinge 34 at head plate 32 defining early-stance flexion axis 36, knee hinge 38 collinear with knee axis 30, and linking member 40 linking early-stance flexion hinge 34 to knee hinge 38. Head plate 32 has anterior end 42 and posterior end 44 that together define head plate axis 46 normal to early-stance flexion axis 36, wherein early-stance flexion axis 36 is between anterior end 42 and posterior end 44. In a specific embodiment, socket 48 at head plate 32 is adjustable in either anterior direction 62 or posterior direction 64.

FIG. 2A is a schematic representation and 2B is a cross-sectional view of artificial knee 20 of FIGS. 1A-1C. Locking hinge assembly 50 defines locking axis 52 and includes footplate 54 having latch 56, and locking hinge 58 collinear with locking axis 52. Pylon connector 60 at footplate 54 is positionable in either anterior direction 62 or posterior direction 64 relative to artificial knee 20.

Post 66 links knee hinge assembly 28 at first end of post 48 with locking hinge assembly 50 at second end 70 of post 66. First end 68 and second end 70 of post 66 define major longitudinal axis 72. Knee hinge 38 and knee axis 30 intersect and are normal to major longitudinal axis 72.

Locking hinge 58 links foot plate 54 to second end 70 of post 66. Locking hinge 58 and locking axis 52 are normal to and intersect line 74 parallel to major longitudinal axis 72. Spring 76 at post 66 provides bias to latch 56 in anterior direction 62, thereby providing bias to rotation of footplate 54 about locking hinge 58 and locking axis 52 in a direction that will engage latch 56 of locking hinge assembly 50 in an interfering relation with linking member 40 of knee hinge assembly 28.

Figure 3A:
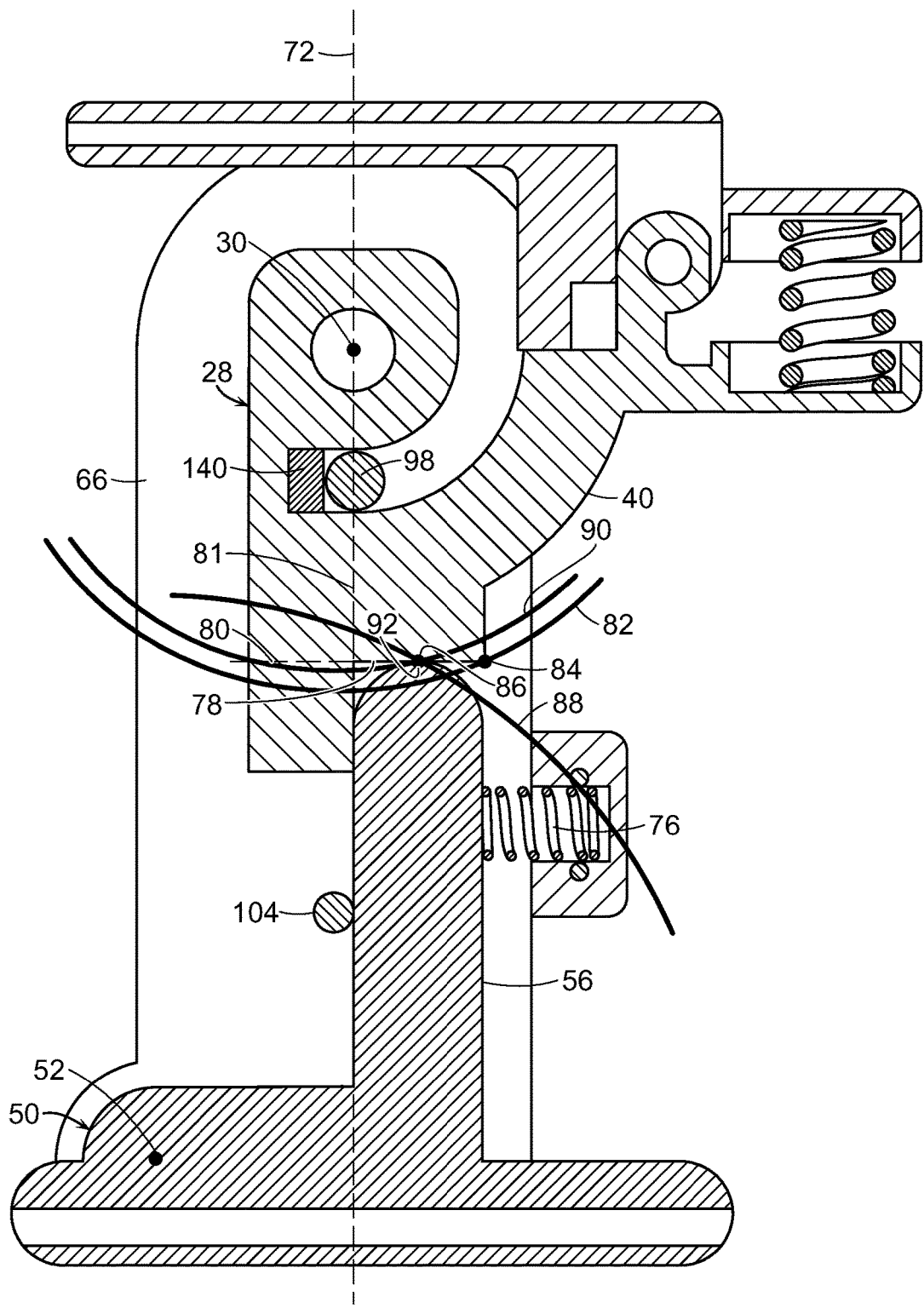
FIG. 3A is a schematic representation of the artificial knee of the invention shown in FIG. 2B.
Figure 3B:
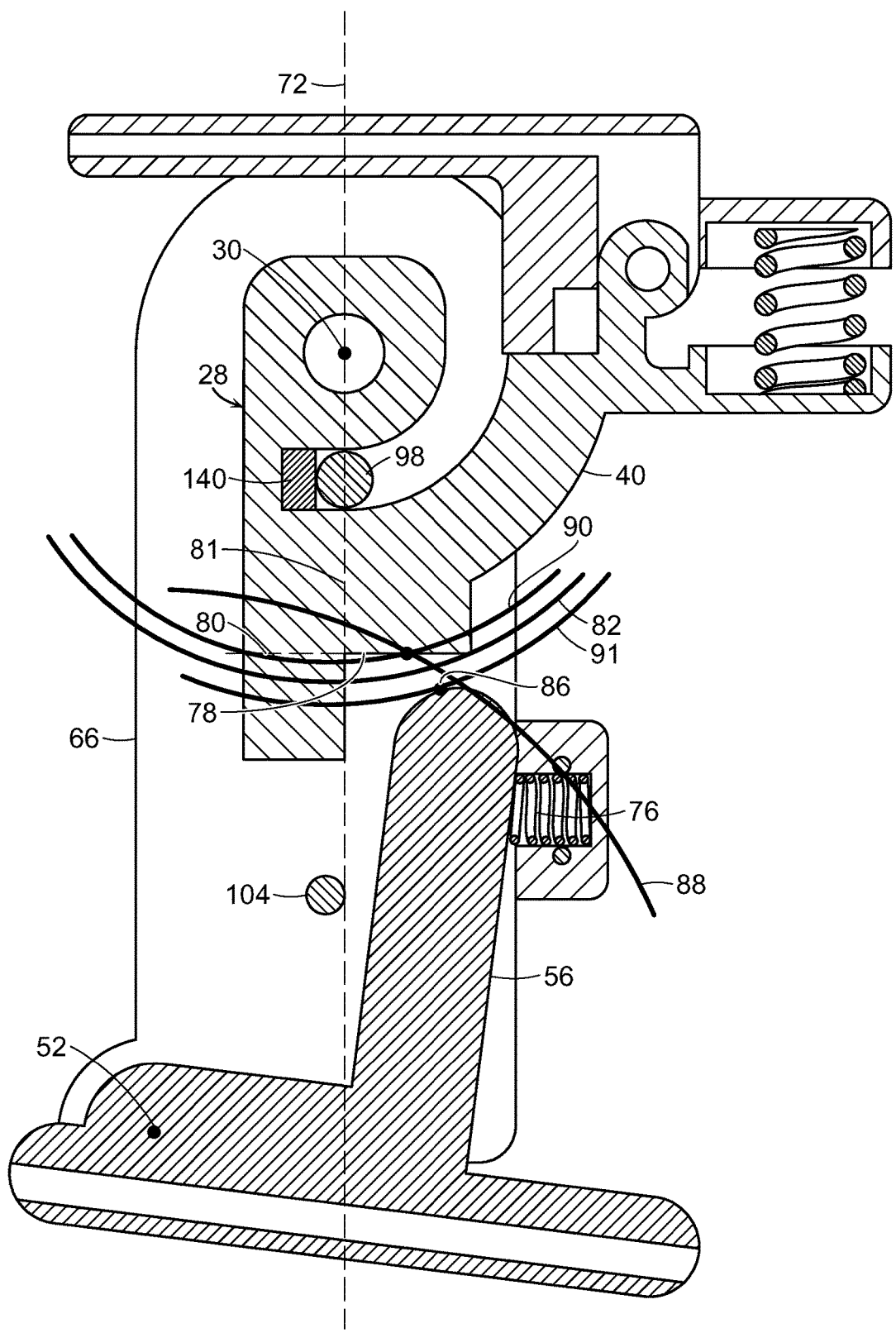
FIG. 3B is the schematic representation of the artificial knee of the invention following rotation of a locking hinge assembly of the artificial knee of the invention at late stance.
Figure 3C:
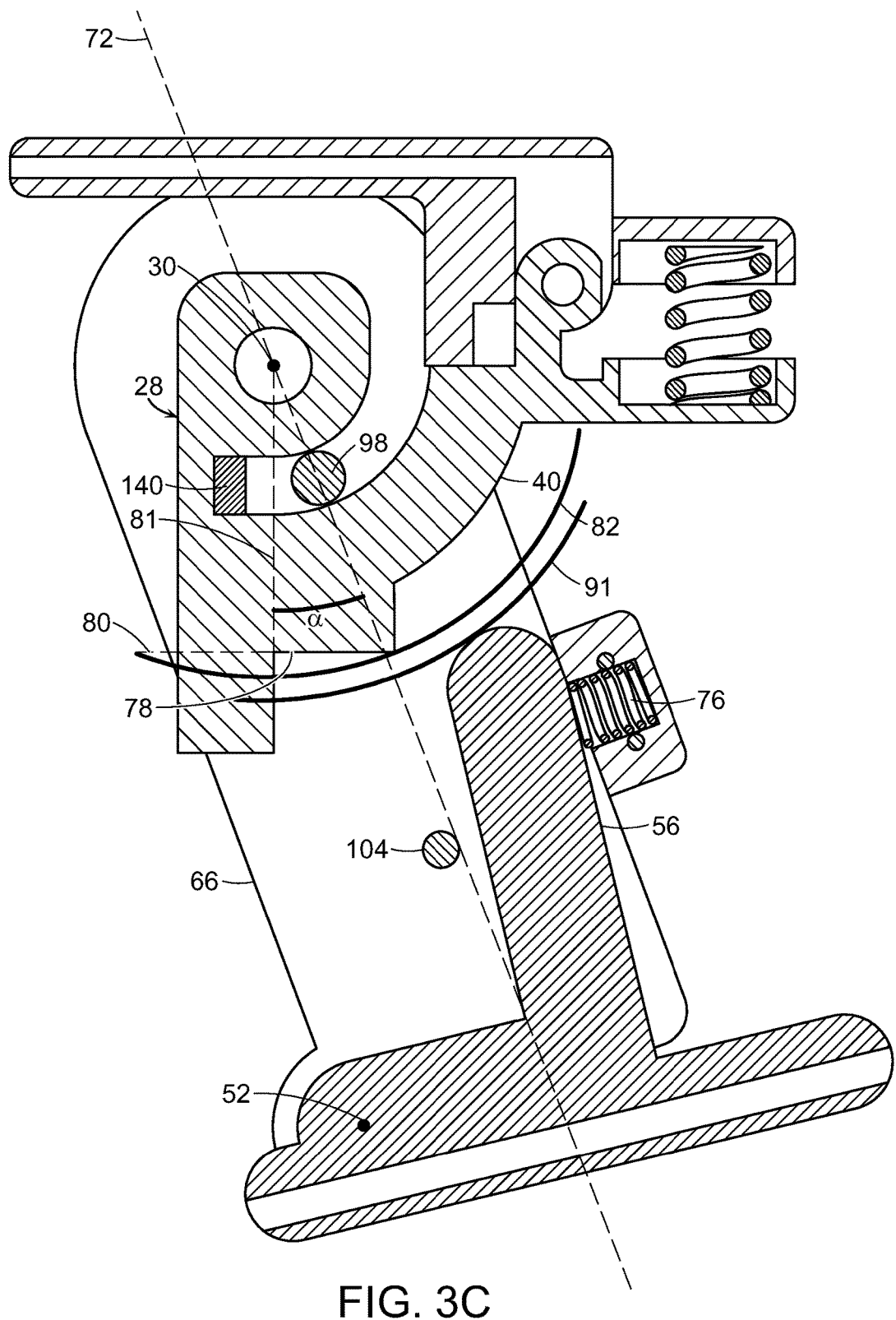
FIG. 3C is the schematic representation of the artificial knee shown in FIGS. 3A and 3B during flexion.

As can be seen in FIGS. 3A-3C, knee hinge assembly 28 defines first locking surface 78 at linking member 40. First locking surface 78 lies in secant line 80 of first circle 82 defined by rotation of post 66 about knee axis 30 at end point 84 of secant line 80. Secant line 80 is normal to radial line 81 that extends from knee axis 30. It should be noted that "radial line," as that term is defined herein, is any line extending radially from the center of a circle, such as knee axis 30, which is the center of first circle 82 and arc 90. "Radial compression," as that term is defined herein, means a compressive force in a radial line. "Radial compression of the knee hinge assembly at the point of interfering relation," therefore, is radial compression in a radial line extending from the point of interfering relation of locking hinge assembly 50 at second locking surface 86 with knee hinge assembly 28 at first locking surface 78. Also, although radial line 81 is shown as being collinear with longitudinal axis 72 in FIGS. 3A and 3B, but with rotation of post 66, longitudinal axis 72 will intersect radial line 81 at angle α. First locking surface 78 also includes end point 84 of secant line 80. Latch 56 of locking hinge assembly 50 defines second locking surface 86 in second circle 88 defined by rotation of latch 56 about locking axis 52. Latch 56 of hinge assembly 50 also defines arc 90 at second locking surface 86 by rotation of post 66 about knee axis 30 that intersects secant line 80 at first locking surface 78, thereby causing an interfering relation at point 92, posterior to knee axis 30, between first locking surface 78 and second locking surface 86 and locking rotation of post 66 about axis 30. Rotation of second locking surface 86 about locking hinge axis 52, as can be seen in FIG. 3B, causes second locking surface 86 to move into non-interfering relation along arc 91 about knee axis 30, as can be seen in FIG. 3C, whereby rotation of post 66 about knee axis 30 is enabled. It should be understood that, in an alternative embodiment, not shown, first locking surface 78 and second locking surface 86 can meet anterior to knee axis 30.

Referring back to FIG. 2B, spring 94 is located between head plate 32 and linking member 40, and biases rotation of linking member 40 about early-stance flexion axis 36 along arc 96 to thereby direct knee hinge 38 and first end 68 of post 66 toward head plate 32. Spring 94 spans head plate 32 and linking member 40 at posterior end 44 of head plate 32, wherein early-stance flexion axis 36 is between the spring 94 and anterior end 42 of head plate 32.

When major longitudinal axis 72 of post 66 is normal to head plate axis 46 (FIG. 1B), line 74, which is parallel to major longitudinal axis 72, intersects locking hinge axis 52 and head plate axis 46 on a side of knee axis 30 opposite to that of early-stance flexion hinge axis 36.

Pin 98 at post 66 engages slot 100 of linking member 40 to thereby limit rotation of post about knee axis 30, thereby preventing hyperextension of artificial knee 20. Further, stop 102 at head plate 32 interferes with rotation of linking member 40 to thereby also prevent hyperextension of artificial knee 20. Stop 104 at post 66 limits rotation of latch 56 about locking axis 52, thereby preventing unintended flexion of artificial knee 20.

Figure 5:
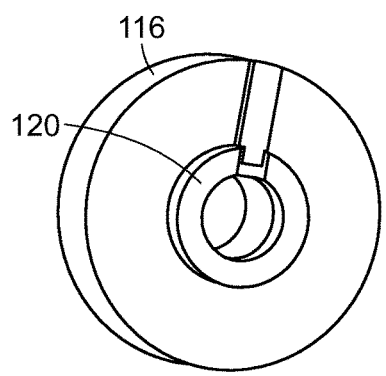
FIG. 5 is a perspective view of a small damper shown in FIG. 4.
Figure 6:
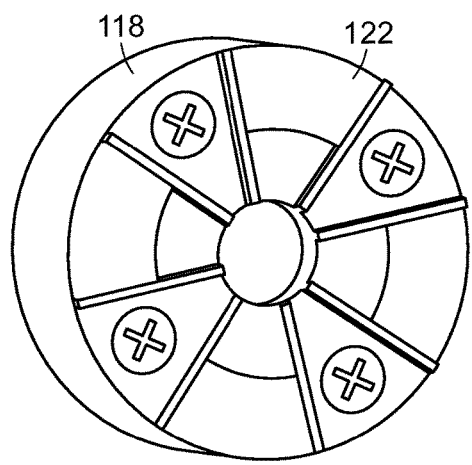
FIG. 6 is a perspective view of a large damper shown in FIG. 4.
Figure 7:
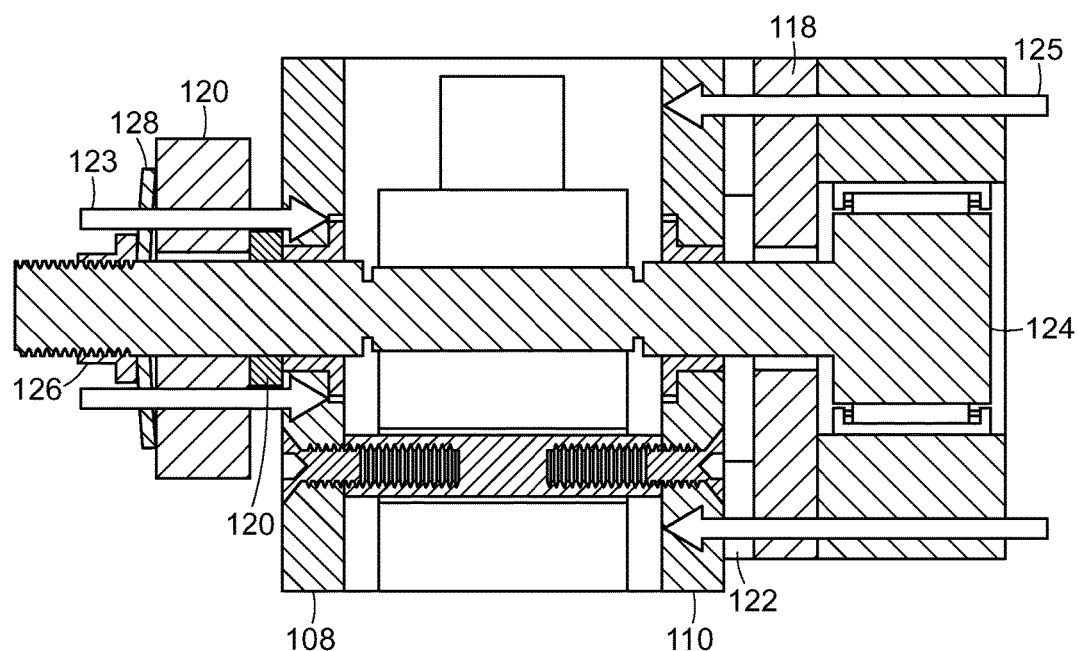
FIG. 7 is a cross-sectional view of the knee hinge assembly and differential damping system of the artificial knee shown in FIGS. 1A-1C.

Referring back to FIGS. 1A-1C, artificial knee 20 includes differential damping system 106. FIG. 4 is an exploded view, in perspective, of differential damping system 106 of artificial knee 20. Post 66 includes first part 108 and second part 110, which are linked by knee hinge 112, and between which are located head plate 32, linking member 40 and locking hinge assembly 50 including latch 56, all of which are also shown in FIGS. 1A-1C, 2A-2B, and 3A-3C. Differential damping system 106 is located at first end 68 of post 66, and is collinear with knee axis 30. Knee hinge 112 includes knee shaft 114 that extends through first end 68 of post 66 and linking member 40, thereby linking post 66 and linking member 40 and allowing rotation of post 66 about knee axis 30 during flexion and extension of artificial knee 20, as will be explained. Differential damping system 106 includes small damper 116 on one side of post 66 and large damper 118 on opposite side of post 66. Both small damper 116 and large damper 118 include friction pads 120,122 (FIGS. 5 and 6) that contact first end 68 of post 66 on respective sides, to thereby provide resistance to rotation of post 66 about knee axis 30 relative to linking member 40 applying normal force 123, 125 to first and second parts 108, 110 of post 66, as shown in FIG. 7. In order to function properly, therefore, knee shaft 114, small damper 116 and large damper 118 do not rotate relative to linking member 40; they are rigidly coupled. Although large damper 118 includes more frictional surface area than that of small damper 116, it is to be understood that, in the alternative, artificial knee 20 could include two dampers, both being of equal frictional surface area, thereby providing equal dampening to rotation of post 66 about knee axis 30.

One-way clutch 124 is located at large damper 118 and, with appropriate hardware, such as lock nut 126 and Belleville washer 128, differential damping system 106 is held together and in place at first end 68 of post 66. High tension (up to as high as 5 kN) in the shaft is made possible by Belleville washers compressed to the rated pre-load by the lock-nut. One-way clutch 124 causes large damper 118 to engage and thereby provide damping resistance to rotation of post 66 at first end 68 relative to linking member 40 in a flexion direction 130 (FIG. 2A) of such rotation, while small damper 116 engages first end 68 of post 66 and consequently provides resistance to rotation of post 66 about knee axis 30 relative to linking member in both flexion direction 130 and extension direction 132 of rotation (FIG. 2A).

As demonstrated by Narang et al. (Y. Narang, "Identification of design requirements for a high-performance, low-cost, passive prosthetic knee through user analysis and dynamic simulation," M.S. thesis, Dept. Mech. Eng., Massachusetts Inst. of Technology, Cambridge, Mass., 2013; Y. Narang and A. Winter, "Effects of prosthesis mass on hip energetics, prosthetic knee torque, and prosthetic knee stiffness and damping parameters required for transfemoral amputees to walk with normative kinematics", *Volume 5A: 38th Mechanisms and Robotics IDETC Conference*, 2014, the relevant teachings of all of which are incorporated by reference in their entirety), the optimal zero-order, or constant-force, damping moment for resisting flexion during late-stance and swing is almost 4 times the value of zero-order damping moment resisting extension during swing (the ratio of $B_{flex}$ (0.29 N-m/kg) to $B_{ext}$ (0.069 N-m/kg)) in Formulas (1) through (3), below. Zero order damping is independent of velocity of operation and is equivalent to a constant frictional force.

The relative size of dampers is determined by the ratio of the damping coefficients ($B_{flex}/B_{ext}$) from the following relations (derived in R. Budynas, J. Nisbett and J. Shigley, *Shigley's mechanical engineering design*. New York: McGraw-Hill, 2011, the relevant teachings of which are incorporated herein by reference in their entirety):

$$T_{flex} = B_{flex}W = \left\{ \frac{2\mu N(R_l^3 - r_l^3)}{3(R_l^2 - r_l^2)} + \frac{2\mu N(R_s^3 r_s^3)}{3(R_s^2 - r_s^2)} \right\} \quad (1)$$

$$T_{ext} = B_{ext}W = \left\{ \frac{2\mu N(R_s^3 - r_s^3)}{3(R_s^2 - r_s^2)} \right\} \quad (2)$$

$$\frac{T_{flex}}{T_{ext}} = \frac{B_{flex}}{B_{ext}} = \left\{ \frac{(R_l^3 - r_l^3)(R_s^2 - r_s^2)}{(R_s^3 - r_s^3)(R_l^2 - r_l^2)} + 1 \right\} \quad (3)$$

where $T_{flex}$ is the total resistive friction torque applied by dampers during flexion of late-stance and swing, $T_{ext}$ is the total resistive friction torque during swing extension (applied only by small damper 116 as large damper 118 does not slip on post 66 and rotates along with post 66), N is the normal force between the damper and post 66, $R_l$ and $r_l$ are the outer and inner diameters respectively of the large damper 118, $R_s$ and $r_s$ are the outer and inner diameters respectively of small damper 116 (FIGS. 4-7), $B_{flex}$ (0.29 N-m/kg) and $B_{ext}$ (0.069 N-m/kg) are the damping coefficients based on a previous study (Narang, Y S. and Winter, A. G., 2014, August. Effects of prosthesis mass on hip energetics, prosthetic knee torque, and prosthetic knee stiffness and damping parameters required for transfemoral amputees to walk with normative kinematics. In ASME 2014 International Design Engineering Technical Conferences and Computers and Information in Engineering Conference (pp. V05AT08A017-V05AT08A017). American Society of Mechanical Engineers, the relevant teachings of which are incorporated by reference in their entirety), W is the body weight of the user in kg, μ is the kinetic coefficient of friction between post 66 (made of aluminum 7075 alloy) and brake pads (which are made of a composite material). The mechanism is tuned to the desired damping values based on the weight of the user. This is achieved by increasing or decreasing tension N in knee shaft 114 by loosening or tightening the lock-nut against Belleville washer 128 on knee shaft 114 (FIGS. 4-7).

In operation, beginning with heel strike, shown in FIGS. 2A and 2B, ground reaction force 134 causes rotation of footplate 54 about locking axis 52 in a direction 136 that causes radial compression of linking member 40 at knee axis 30. Spring 76 provides bias to latch 56 to ensure engagement of first locking surface 78 and second locking surface 86 in interfering relation, as shown in FIG. 3A, through the early-stance gait phase of an individual wearing artificial knee. Stop 104 limits rotation of latch 56 and, thus, of footplate 54 about locking axis 52. As can be seen in FIG. 2A, ground reaction force 134 during the engagement of latch 56 with linking member 40 is posterior to locking axis 52, knee axis 30 and early-stance phase axis 36.

Figures 8A, 8B:
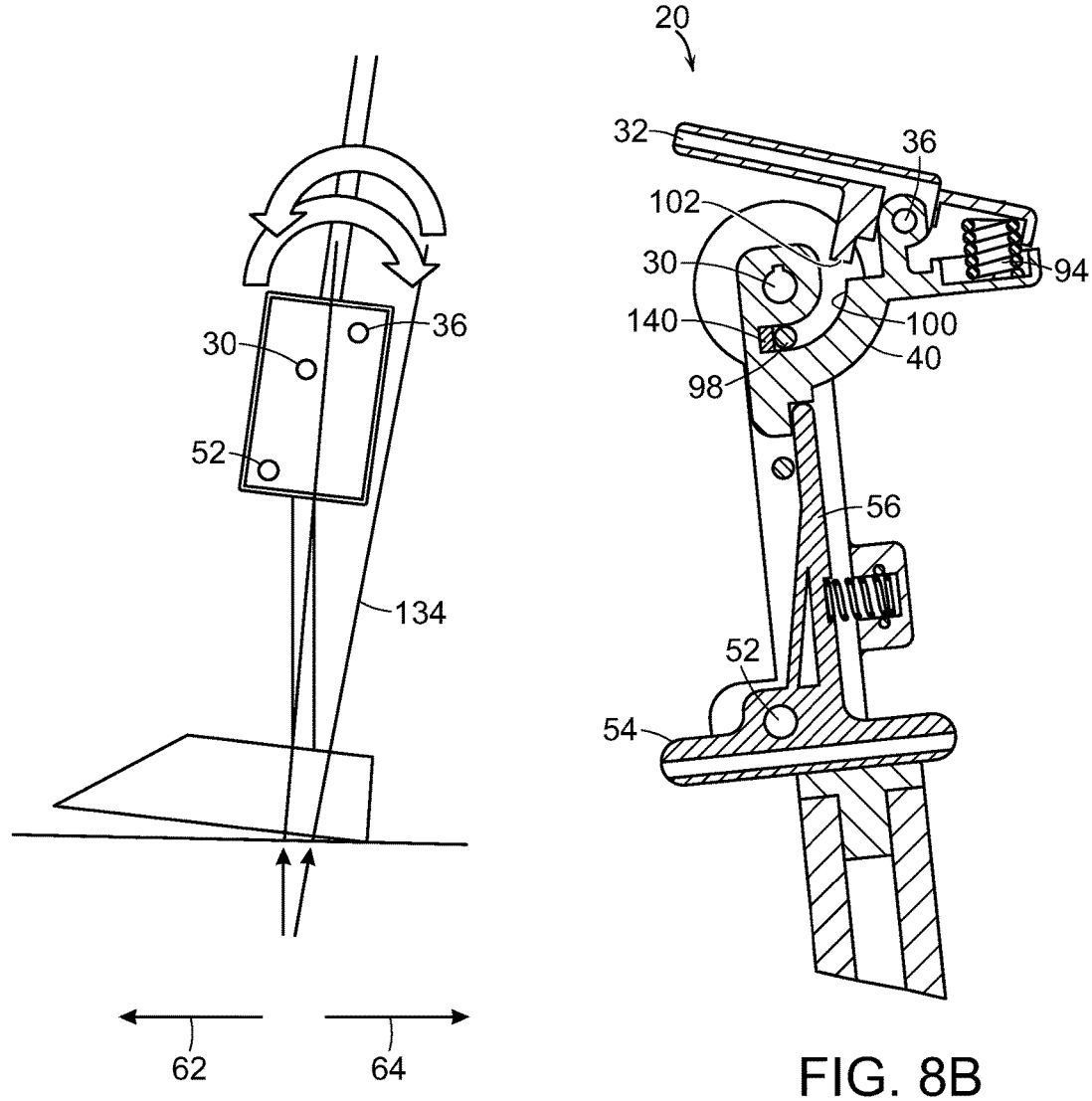
FIG. 8A is a schematic representation of shifting of ground reaction force during early-stance of the artificial limb shown in FIG. 1A.
FIG. 8B is a cross-sectional view of the artificial knee shown in FIGS. 1A-1C during early-stance flexion of the artificial knee.

Ground reaction force 134 provides a flexion moment about knee axis 30 and locking axis 52 at heel strike, whereby linking member 40 rotates in flexion relative to head plate 32 about early-stance phase axis 36, thereby compressing spring 94. As the individual wearing artificial knee 20 passes from heel strike to the early-stance phase, ground reaction force 134 moves from a position posterior to early-stance phase axis 36 to a position anterior to early-stance phase axis 36, while still posterior to knee axis 30, as shown in FIGS. 8A and 8B. As ground reaction force 134 travels anterior to early-stance flexion axis 36, spring 94 provides an extension moment to artificial knee 20 about early-stance flexion axis 36. During this early-stance extension movement about early-stance flexion axis 36, spring 94 releases energy stored from early-stance flexion. This early-stance flexion-extension can significantly reduce metabolic expenditure because residual hip muscles of the individual do not need to apply a resistive moment during early-stance flexion and an active moment during early-stance extension. Also, able-bodied kinematics are enabled because of this elastic cushioning in the knee at heel strike. Preferably, rotation about early-stance flexion axis 36 is limited to an angle of about 20°. In one embodiment, based on a K-stance coefficient of 2.89 N-m/kg/rad, a spring-stiffness of 270 kN/m is selected to provide the required torsional stiffness about early-stance flexion axis 36. Also, in a preferred embodiment, lever arm between early-stance flexion axis 36 and spring 94 is provided by a slot, which facilitates tuning of torsional stiffness for a range of equivalent able-bodied body-weight range, such as between about 50 kg to about 90 kg, including the weight of artificial knee. Extension of artificial knee 20 continues so long as ground reaction force 134 is posterior to locking hinge axis 52 and so long as latch 56 is engaged with linking member 40, but is terminated by stop 102 at head plate 32, thereby terminating rotation of linking member 40 about early-stance flexion axis 34, and by stop 140 at linking member, thereby limiting travel of pin 98 through slot 100 of linking member 40 at post 66. While ground reaction force 134 is posterior to knee axis 30, linking member 40 and latch 56 are in compression between knee axis 30 and locking hinge axis 52, as shown in FIG. 3A.

Figure 9B:
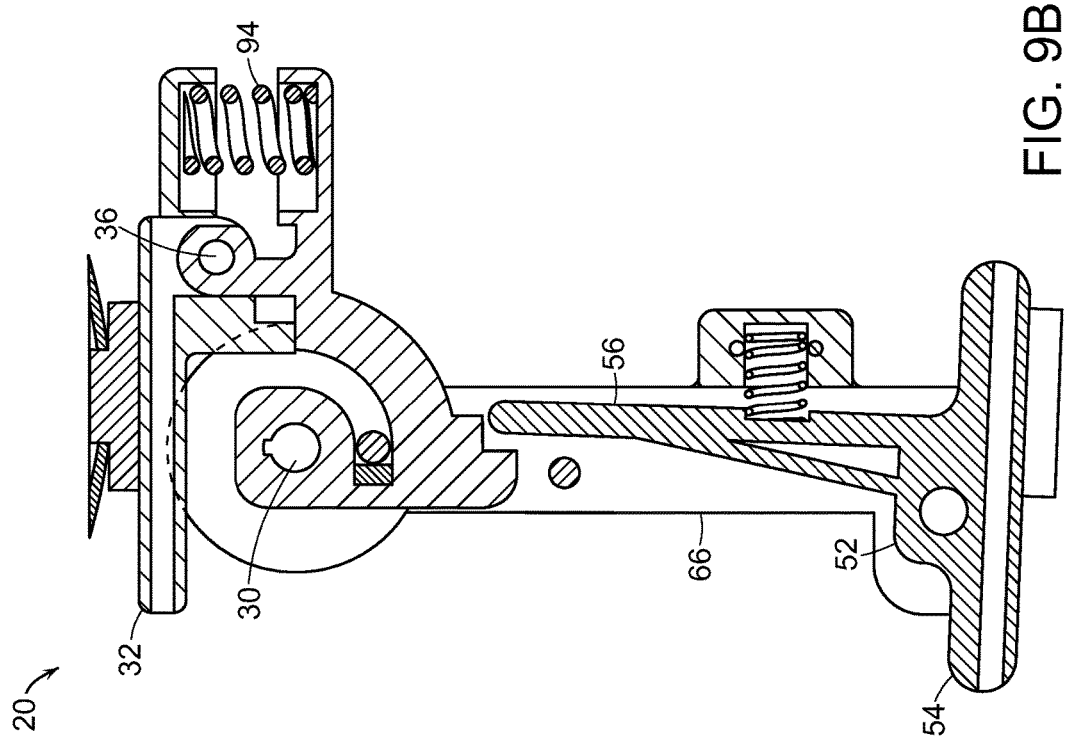
FIG. 9B is a cross-sectional view of the artificial knee of FIGS. 1A-1C during mid-stance to late-stance.
Figure 9A:
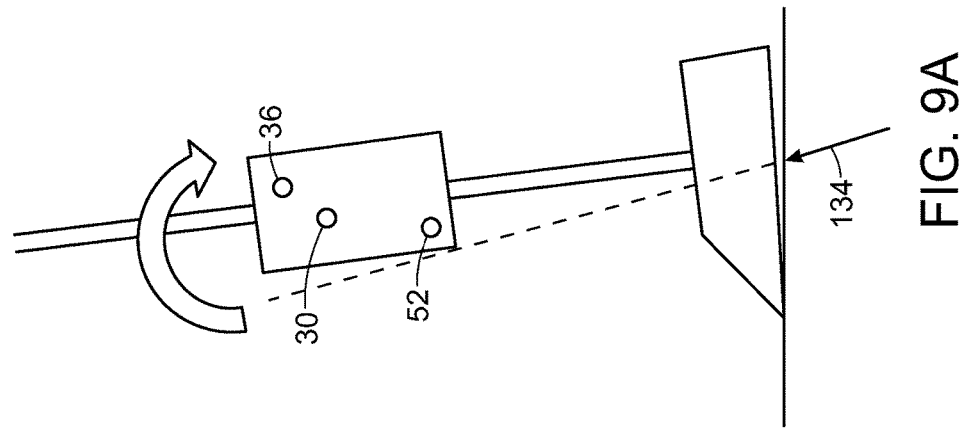
FIG. 9A is a schematic representation of ground reaction force of the artificial limb of FIG. 1A during mid-stance to late-stance.
Figure 10B:
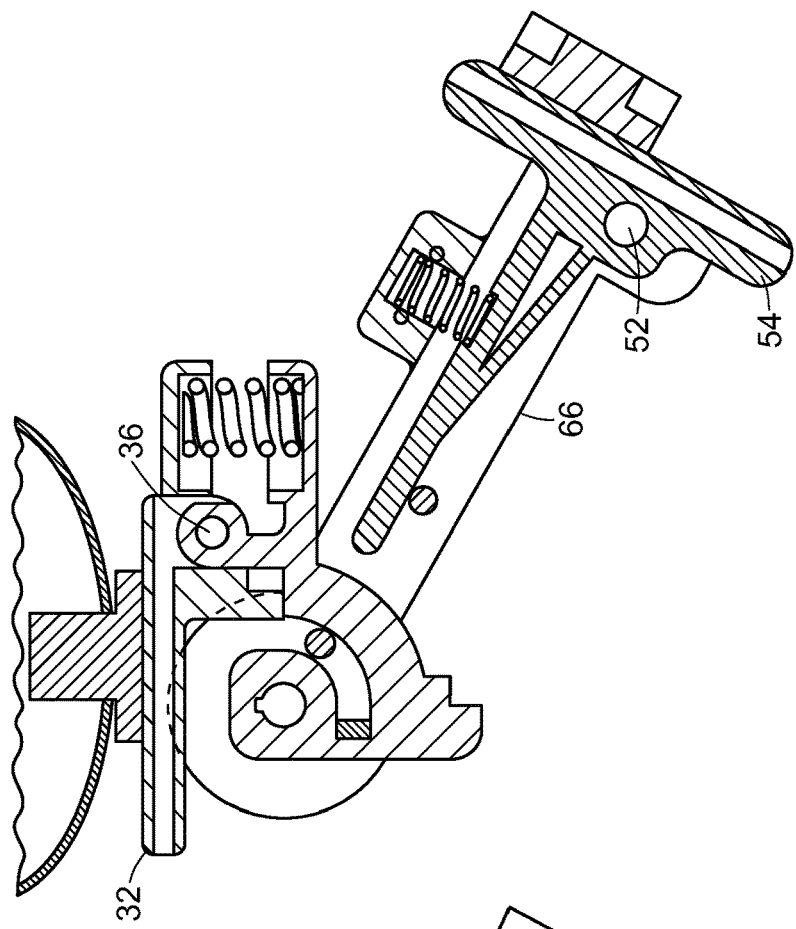
FIG. 10B is a cross-section view of the artificial knee of FIGS. 1A-1C during swing phase.
Figure 10A:
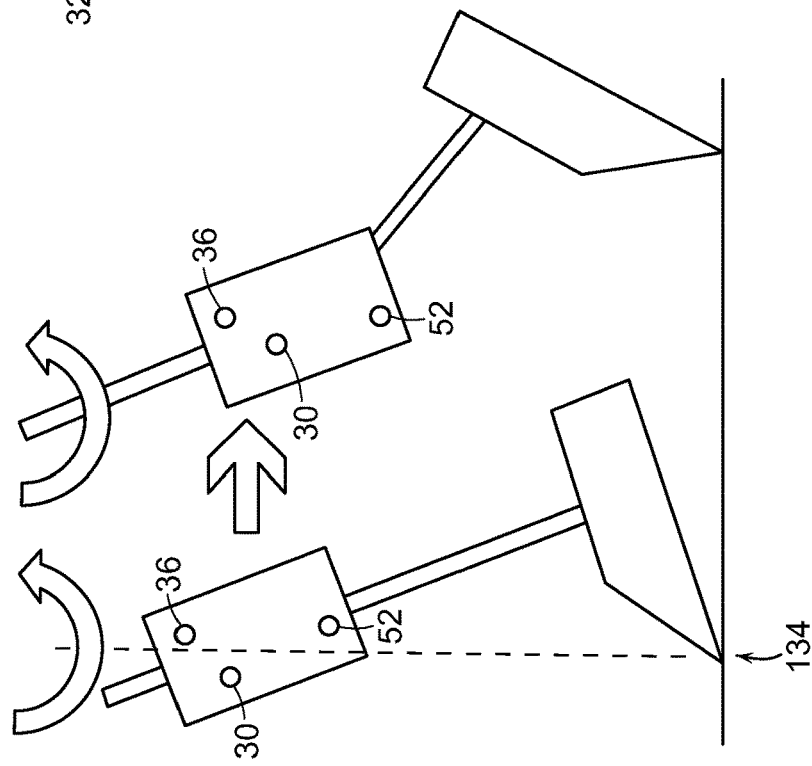
FIG. 10A is a schematic representation of ground reaction force on the artificial knee of FIGS. 1A-1C during late-stance and early swing phases.

As shown in FIG. 9A and FIG. 9B, continued advancement of the individual past mid-stance causes ground reaction force 134 to move anterior to knee axis 30 and then locking axis 52. Movement of ground reaction force 134 anterior to locking axis 52 causes rotation of footplate 54 about locking axis 52 and disengagement of latch 56 from interfering relation with linking member 40, thereby compressing spring 76, as can be seen in the transition from FIG. 3A to FIG. 3B.

When the individual causes artificial knee 20 to enter late stance, ground reaction force 134 moves to a point anterior to locking axis 52 but posterior to knee axis 30, as shown in FIG. 9B, whereby post 66 and locking hinge assembly 50, now disengaged from linking member 40, as shown in FIGS. 3B and 9B, rotates about knee axis 30 in knee flexion, as shown in the transition from FIG. 3B to FIG. 3C, and from FIGS. 9A and 9B to FIGS. 10A and 10B. During knee flexion, damper 116 and damper 118 are both engaged, thereby providing resistance to rotation of post 66 and locking hinge assembly 50 about knee axis 30.

During flexion of artificial knee 20, head plate 32 and linking member 40 do not move relative to each other because spring 94 prevents flexion about early-stance flexion axis 36. In one embodiment, mechanical contact between linking member 40 and latch 56 serves as a hard stop to prevent any accidental flexion over 90° during swing phase.

It is understood that normal knee flexion during swing is about 65°.

Following flexion, post 66 and locking hinge 58 begin extension of artificial knee 20, thereby disengaging large damper 118 by disengagement of one-way clutch 124 at knee axis 30. Extension of artificial knee 20 continues until heel strike, when ground reaction force 134 at heel strike causes footplate 54 to rotate about locking axis 52 to thereby reengage latch 56 of locking hinge assembly 50 with linking member 40, as shown in FIGS. 2A and 2B, and in FIG. 3A, to thereby repeat the gait cycle as the individual proceeds to walk.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. An artificial knee, comprising:
   a) a knee hinge assembly defining a knee axis, the knee hinge assembly including (i) a head plate, (ii) an early-stance flexion hinge at the head plate defining an early-stance flexion axis, the head plate having an anterior end and a posterior end that together define a head plate axis normal to the early-stance flexion axis, the early-stance flexion axis being between the anterior end and the posterior end, (iii) a knee hinge collinear with the knee axis at a post, the post having a first end and a second end that together define a major longitudinal axis, the knee axis intersecting and being normal to the major longitudinal axis, and (iv) a linking member that links the early-stance flexion hinge to the knee hinge and defines a first surface that contacts a locking hinge assembly during compression of the locking hinge assembly and the knee hinge assembly;
   b) the locking hinge assembly defining a locking axis;
   c) the post linking the knee hinge assembly and the locking hinge assembly, wherein a ground reaction force applied to the artificial knee posterior to the locking axis causes an interfering relation at a point between the locking hinge assembly and the knee hinge assembly during heel strike and early stance gait phases of an individual wearing the artificial knee, whereby rotation of the locking hinge assembly causes radial compression of the knee hinge assembly at the point of interfering relation, thereby locking rotation of the post about the knee axis, and wherein shifting of the ground reaction force anterior to the locking axis during a mid-stance gait phase of the individual causes rotation of the post about the locking axis, thereby unlocking rotation of the post about the knee axis; and d) a spring between the head plate and the linking member biasing rotation of the linking member about the early-stance flexion axis to thereby direct the knee hinge and the first end of the post toward the head plate.

2. The artificial knee of claim 1, wherein the locking hinge assembly includes:
   a) a foot plate having a latch, the latch defining a second surface that contacts the first surface of the knee hinge assembly at or posterior to the major longitudinal axis during compression of the locking hinge assembly and the knee hinge assembly; and
   b) a locking hinge collinear with the locking axis and linking the foot plate to the second end of the post.

3. The artificial knee of claim 2, wherein the locking axis is normal to and intersects a line that is parallel to the major longitudinal axis.

4. The artificial knee of claim 3, wherein, when the major longitudinal axis of the post is normal to the head plate axis, the line parallel to the major longitudinal axis intersects the head plate axis on a side of the knee axis opposite that of the early-stance flexion hinge axis.

5. The artificial knee of claim 4, wherein the spring spans the head plate and the linking member at the posterior end of the head plate, and wherein the early-stance flexion axis is between the spring and the anterior end of the head plate.

6. The artificial knee of claim 5, further including a differential damping system at the knee hinge, wherein the differential damping system includes:
   a) a first damper at one side of the knee hinge, the first damper engaging the post and the linking member;
   b) a second damper at an opposite side of the knee hinge, the second damper engaging the post and the linking member; and
   c) a one-way clutch that engages the second damper only during flexion of the artificial knee.

7. The artificial knee of claim 6, wherein the second damper provides more resistance to rotation of the post about the knee axis than does the first damper.

8. The artificial knee of claim 1, wherein:
   a) the knee hinge assembly further defines a first locking surface that lies in and includes an endpoint of a secant line of a first circle defined by rotation of the post about the knee axis, wherein the secant line is normal to a radial line extending from the knee axis to the first circle;
   b) the locking hinge assembly further defines a second locking surface that lies in a second circle defined by rotation about the locking axis; and
   c) the locking hinge assembly defines an arc at the second locking surface by rotation of the post about the knee axis, the knee axis intersecting the secant line at the first locking surface, whereby rotation of the second locking surface about the locking axis causes the radial compression of the knee hinge assembly at a given point between the first locking surface and the knee axis, thereby causing the interfering relation between the first locking surface and the second locking surface that locks the post and prevents rotation of the post about the knee axis.

9. An artificial knee, comprising:
   a) a head plate, having an anterior end and a posterior end defining a head plate axis, and an early-stance flexion hinge between the anterior end and the posterior end defining an early-stance flexion axis that is normal to the head plate axis;
   b) a post having
      i) a first end and a second end together defining a major longitudinal axis,
      ii) a knee hinge defining a knee axis at the first end of the post, wherein the knee axis is normal to and intersects the major longitudinal axis, and
      iii) a locking hinge defining a locking axis at the second end of the post, wherein the locking axis is normal to and intersects a line parallel to the major longitudinal axis;
   c) a linking member linked to the head plate at the early-stance flexion hinge and linked to the post at the knee hinge, wherein, when the major longitudinal axis of the post is normal to the head plate axis, the line parallel to the major longitudinal axis intersects the head plate axis on a side of the knee axis opposite to that of the early-stance flexion axis;
   d) a spring between the head plate and the linking member biasing rotation of the linking member about the early-stance flexion axis to thereby direct the knee hinge and the first end of the post toward the head plate; and
   e) a foot plate linked to the post at the locking hinge, the foot plate including a latch that is in an interfering relation at a point between the latch and the linking member during heel strike and early stance gait phases of an individual wearing the artificial knee, whereby the latch will be engaged with the linking member thereby causing radial compression of the knee hinge assembly at the point of interfering relation, and preventing rotation of the post about the knee axis, and whereby, during a mid-stance gait phase of the individual, when a ground reaction force applied to the artificial knee is anterior to the locking axis, the foot plate will rotate about the locking axis and consequently disengage the latch from the linking member, thereby enabling the post to rotate about the knee axis.

10. The artificial knee of claim 9, wherein the interfering relation between the latch and the linking member during heel strike and early-stance gait phases is posterior to the major longitudinal axis.

11. The artificial knee of claim 10, wherein the spring spans the head plate and the linking member at the posterior end of the head plate, and the early-stance flexion axis is between the spring and the anterior end of the head plate.

12. The artificial knee of claim 11, further including a differential damping system at the knee hinge, wherein the differential damping system includes:
   a) a first damper at one side of the knee hinge, the first damper engaging the post and the linking member;
   b) a second damper at an opposite side of the knee hinge, the second damper engaging the post and the linking member; and
   c) a one-way clutch that engages the second damper only during flexion of the artificial knee.

13. The artificial knee of claim 12, wherein the second damper provides more resistance to rotation of the post about the knee axis than does the first damper.

* * * * *